(12) United States Patent
Holmqvist et al.

(10) Patent No.: US 8,870,831 B2
(45) Date of Patent: Oct. 28, 2014

(54) DOSE RESET MECHANISM

(75) Inventors: Anders Holmqvist, Värmdö (SE); Anders Wieselblad, Stockholm (SE)

(73) Assignee: SHL Group AB, Nacka Strand (SE)

( * ) Notice: Subject to any disclaimer, the term of this patent is extended or adjusted under 35 U.S.C. 154(b) by 282 days.

(21) Appl. No.: 13/392,143

(22) PCT Filed: Aug. 24, 2010

(86) PCT No.: PCT/SE2010/050910
§ 371 (c)(1),
(2), (4) Date: Mar. 14, 2012

(87) PCT Pub. No.: WO2011/025448
PCT Pub. Date: Mar. 3, 2011

(65) Prior Publication Data
US 2012/0165752 A1 Jun. 28, 2012

(30) Foreign Application Priority Data
Aug. 24, 2009 (SE) .................................. 0950600

(51) Int. Cl.
*A61M 5/00* (2006.01)
*A61M 5/315* (2006.01)
*A61M 5/20* (2006.01)

(52) U.S. Cl.
CPC .............. *A61M 5/31593* (2013.01); *A61M 5/20* (2013.01); *A61M 5/31586* (2013.01); *A61M 5/31575* (2013.01); *A61M 2005/202* (2013.01); *A61M 5/31556* (2013.01); *A61M 5/3156* (2013.01); *A61M 5/31553* (2013.01); *A61M 5/31535* (2013.01)
USPC .............................. 604/211; 604/209; 604/135

(58) Field of Classification Search
CPC ..................... A61M 5/31533; A61M 5/31535; A61M 5/31541; A61M 5/31543; A61M 5/31545; A61M 5/31548; A61M 5/3155; A61M 5/31551; A61M 5/315553
USPC .......... 604/131, 134, 135, 207, 208, 209, 211
See application file for complete search history.

(56) References Cited

U.S. PATENT DOCUMENTS

| 2004/0199117 A1 | 10/2004 | Giambattista et al. |
| 2008/0147005 A1* | 6/2008 | Moller et al. .................. 604/134 |

FOREIGN PATENT DOCUMENTS

| WO | 2006/045526 A1 | 5/2006 |
| WO | 2007/063342 A1 | 6/2007 |

OTHER PUBLICATIONS
Swedish Patent Office, Int'l Search Rpt in PCT/SE2010/050910, Dec. 8, 2010.
Swedish Patent Office, Written Opinion in PCT/SE2010/050910, Dec. 8, 2010.

* cited by examiner

*Primary Examiner* — Bhisma Mehta
*Assistant Examiner* — Nicholas Meghri
(74) *Attorney, Agent, or Firm* — Piedmont Intellectual Property

(57) ABSTRACT

A dose reset mechanism for a medicament delivery device with a housing and a medicament container includes a dose setting member in the housing for setting a dose when it is rotated and for resetting the dose when it is rotated in the opposite direction. The dose setting member has a drive member connected to a plunger rod such that when the drive member rotates, the rod moves axially; and a connection member between the dose setting member and the drive member. A ratchet mechanism enables the connection member to rotate when the dose setting member rotates for setting a dose but not to move in the opposite direction. At least one dose reset member and at least one blocking member are connected to the ratchet mechanism such that the connection member and drive member are released when a dose knob is turned in the opposite direction.

13 Claims, 5 Drawing Sheets

DOSE RESET MECHANISM

TECHNICAL AREA

The present invention relates to a reliable dose reset mechanism intended to be used in a medical delivery device, and in particular a device where the dose to be delivered by the medical delivery device can be set.

TECHNICAL BACKGROUND

In many instances it is desirable that the medicament delivery device is capable of delivering a certain specified quantity of the medicament. This is for example the case with a multi-dose injection device, which is capable of delivering a number of specified, set, doses until the compartment is empty. One example is disclosed in the European patent application publication No. EP 1 218 042, where specific doses can be set before injection by turning a dose setting button on the distal end of the injector.

If however a dose is set too high, i.e. the user overshoots the desired dose, the device has to be reset so that a user may set the proper dose. According to EP 1 218 042 this is done by continuing the rotation of the dose setting knob until it is moved past the maximum value, past which the dose setting knob is released. It is then possible to rotate back the dose setting knob to the initial, or zero, position, at which position the dose setting knob is re-connected to the dose setting mechanism.

A clear drawback with the solution according to EP 1 218 042 is that if the dose is overshot, the dose knob has to be rotated the whole way to the end position and then rotated back to the zero position, and then again turned to the desired dose. Thus, if a dose setting is missed a lot of rotation is required in order reset the device and set the dose. Further the design requires a number of inter-acting components in order to achieve the desired function.

WO 2006/045526 relates to a device employing a so called dial-down mechanism to reduce a set dose in incremental steps. During dial-up, i.e. increasing the dose, WO 2006/045526 relies on an arm to slide over teeth arranged on the inside of a nut in order to flex against the teeth in a locking state upon arrival at the preferred dose.

The drawback of this solution is that as the arm slides against the teeth it will eventually wear down and the force bias against the teeth, which is based on the inherent material properties and the design of the arm, will be reduced over time, resulting in reduced reliability of the locking mechanism of the arm against the teeth. Also, since WO 2006/045526 uses a curved profile for the teeth and for the connecting member of the flexible arm this reliability problem is worsened.

There are thus a number of aspects that are addressed with the present invention.

BRIEF DESCRIPTION OF THE INVENTION

The aim of the present invention is to provide a dose reset mechanism that is reliable, easy and intuitive for a user to handle and which does not require a plurality of interacting components for performing the function.

This aim is obtained according to the present invention by the features of the independent patent claim.

Preferable embodiments of the present invention form the subject of the dependent patent claims.

According to a major aspect of the invention, it is characterised by a dose reset mechanism to be used in a medicament delivery device comprising a housing having opposite distal and proximal ends and a container in which medicament is stored, wherein the dose reset mechanism comprises a dose setting member coaxially and rotationally arranged in said housing for setting a dose when it is rotated and for resetting the dose when it is rotated in the opposite direction, said dose setting member having a dose setting knob accessible outside the distal end of said housing, a drive member connected to a plunger rod to act on said container for expelling the medicament, a connection member arranged between said dose setting member and said drive member, wherein said connection member and said dose setting member are connected to each other by engagement means and wherein said connection member and said drive member are interconnected by ratchet means such that said connection member is also rotated when said dose setting knob is rotated for setting a dose but locked by the ratchet means from being moved in the opposite direction, a drive spring having a first end connected to the connection member and a second end connected to a fixed point of said housing such that said drive spring is tensioned when said dose setting member and said connection member are rotated for setting a dose, wherein said dose setting member further comprises at least one dose reset member and at least one supporting element interactively connected to said ratchet means such that said ratchet interconnection between said connection member and said drive member is released when said dose knob is turned in the opposite direction.

According to another aspect of the invention said drive member is threadedly connected to the plunger rod such that when said drive member is rotated, said plunger rod is axially moved to expel said medicament.

According to yet another aspect of the invention said ratchet means comprises a number of generally radial inwardly extending ledges on the distal inner circumferential surface of said drive member, and generally radial outwardly protruding ledges arranged on flexible arms extending in the circumferential direction of the connection member.

According to a further aspect of the invention said at least one dose reset member comprises a first arm portion protruding generally transversal to the outer circumferential surface of said dose setting member, and a second arm portion axially extending towards the proximal direction, and wherein said second arm portion is arranged with a curved surface.

According to another aspect of the invention each ledge on the flexible arms of the connection member is arranged with one side surface having a curved shape and arranged to cooperate with the curved surface of the second arm portion of the reset member.

According to another aspect of the invention said connection member comprises at least one cut-out forming a slot that extends in a circumferential direction of the connection member and is limited in the circumferential directions by transversal walls of the at least one cut-out and in the radial direction by the circumferential wall of the cut-out and by the flexible arm.

According to another aspect of the invention said at least one cut-out comprises a closed end from which the flexible arm extends and an open end forming a gap between the ledge and one of the transversal walls of the slot.

According to another aspect of the invention said at least one supporting element comprises a first portion protruding generally transversal to the outer circumferential surface of said dose setting member, and a second portion axially extending towards the proximal direction into the slot, is capable of locking said outwardly protruding ledges in engagement with said inwardly extending ledges when the supporting element is positioned adjacent the outwardly protruding ledge.

According to another aspect of the invention said dose setting member is movable between a neutral position in which the supporting element is positioned in the slot adjacent the outwardly protruding ledges and a reset position in which the supporting element is positioned in the gap at the open end of the slot.

According to another aspect of the invention said dose setting member is also movable between the neutral position and a dose setting position in which the supporting element is positioned in the closed end of the slot.

According to another aspect of the invention an engagement means comprises at least one dose setting drive member having a first part protruding generally transversal to the outer circumferential surface of said dose setting member and a second part axially extending towards the proximal direction, and at least one cut-out provided on the outer circumferential surface connection member such that the position of said at least one cut-out corresponds to the position of the at least one drive member, whereby the drive member fits in the cut-outs.

According to another aspect of the invention the width of the at least one cut-out is somewhat larger than the width of the at least one drive members.

According to another aspect of the invention flexible return elements are circumferentially arranged in the cut-outs, between at least one transversal wall of the cut-outs and the dose setting driver members, capable of returning the dose setting member to the neutral position.

According to a yet further aspect of the invention a medicament delivery device comprises a dose reset mechanism according to anyone of the above mentioned aspects.

There is a clear advantage that the dose can be reset in a safe and easy way by merely turning the dose setting knob in the opposite way, which then causes the dose setting mechanism to be moved only one increment at the time. Thus the reset movement is performed in a very controlled way. A further advantage is that the function is performed with a few components, thereby adding very little to the total cost of the device. Another advantage is the improved reliability and lifetime of the device due to the safe locking of the set dose.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
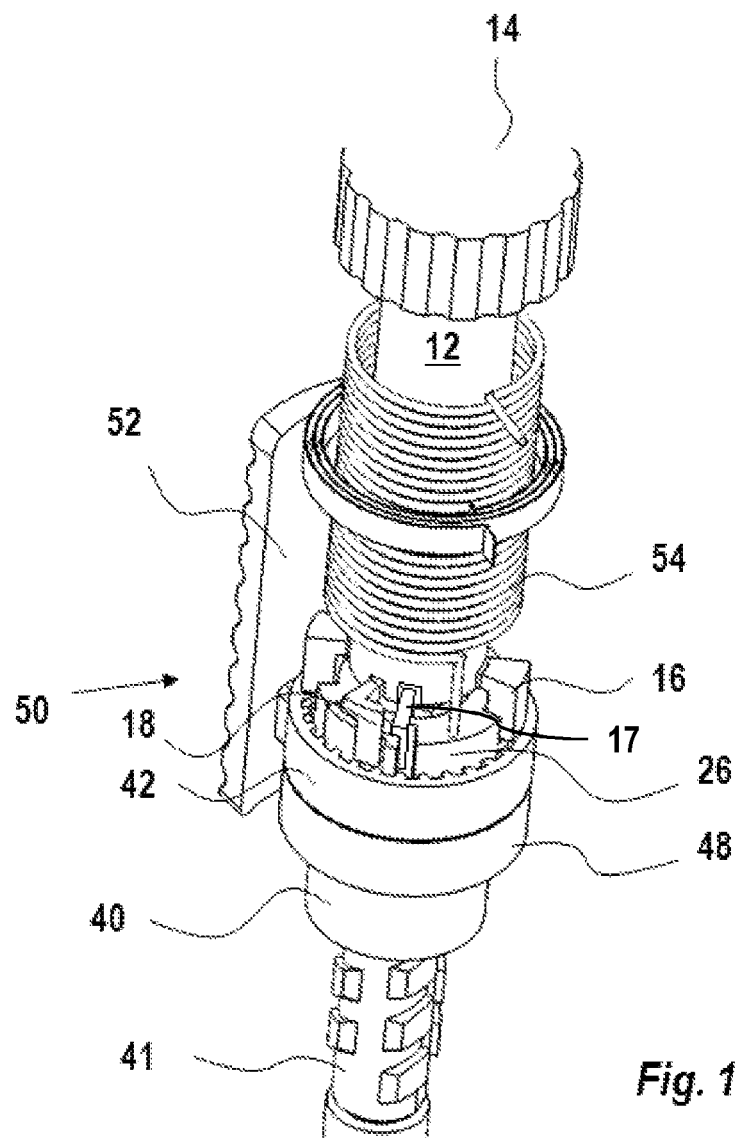
FIG. 1 is a detailed view in perspective of the dose reset mechanism according to the present invention.

In the present application, when the term "distal part/end" is used, this refers to the part/end of the medicament delivery device, or the parts/ends of the members thereof, which under use of the medicament delivery device is located the furthest away from the medicament delivery site of the patient. Correspondingly, when the term "proximal part/end" is used, this refers to the part/end of the medicament delivery device, or the parts/ends of the members thereof, which under use of the medicament delivery device is located closest to the medicament delivery site of the patient.

The dose reset mechanism according to the invention shown in the drawings is intended to be used in a medicament delivery device such as an injector, an inhaler, a nebulizer or the like having a device housing. The housing and other components of the device that do not form part of the invention are removed in the drawings for clarity. The dose reset mechanism to be used in a medicament delivery device comprises a housing having opposite distal and proximal ends and a container in which medicament is stored, wherein the dose reset mechanism also comprises:

a dose setting member (10) coaxially and rotationally arranged in said housing for setting a dose when it is rotated and for resetting the dose when it is rotated in the opposite direction, said dose setting member having a dose setting knob (14) accessible outside the distal end of said housing;

a drive member (38) connected to a plunger rod (41) to act on said container for expelling the medicament;

a connection member (26) arranged between said dose setting member (10) and said drive member (38), wherein said connection member and said dose setting member are connected to each other by engagement means (16, 30), and wherein said connection member and said drive member are interconnected by ratchet means (34, 44) such that said connection member is also rotated when said dose setting knob is rotated for setting a dose but locked by the ratchet means from being moved in the opposite direction;

a drive spring (54) having a first end connected to the connection member and a second end connected to a fixed point of said housing such that said drive spring is tensioned when said dose setting member and said connection member are rotated for setting a dose; wherein said dose setting member (10) further comprises at least one dose reset member (18) and at least one supporting element (17) interactively connected to said ratchet means (34, 44) such that said ratchet interconnection (34, 44) between said connection member and said drive member is released when said dose knob is turned in the opposite direction.

The ratchet means comprises a number of generally radial inwardly extending ledges 44 on the distal inner circumferential surface of said drive member 38, and generally radial outwardly protruding ledges 34 arranged on the free ends of flexible arms 32 that extend in the circumferential direction of the connection member.

Figure 2:
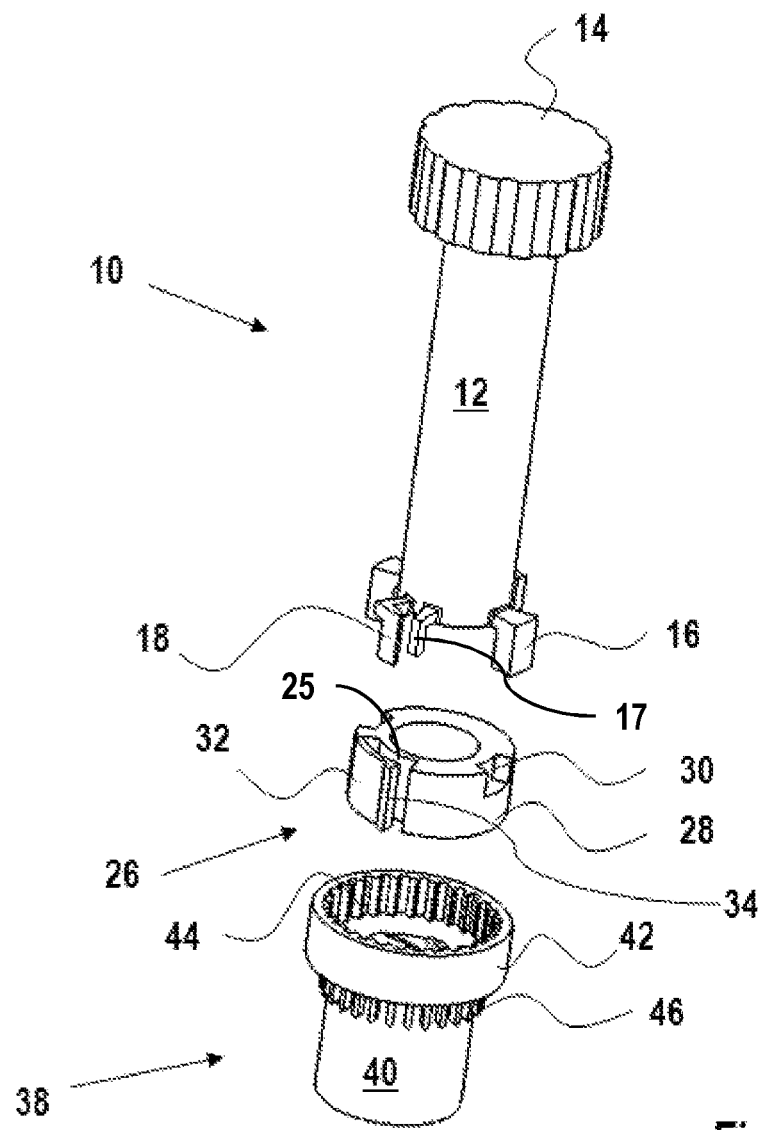
FIG. 2 is an exploded view of the key components of the dose reset mechanism according to the present invention.
Figure 4:
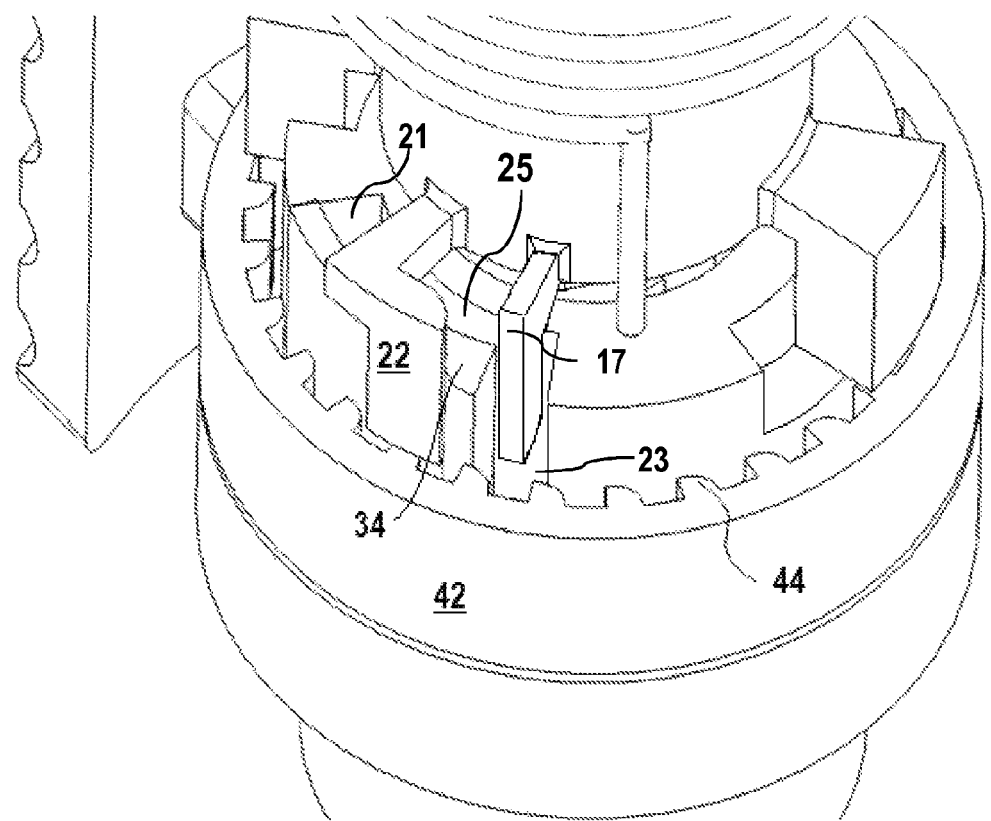
FIG. 4 is a detailed view of the dose reset mechanism when the reset movement has been initiated.

A cut-out in the connection member 26 forms a slot 25, FIG. 2, which extends in a circumferential direction of the connection member. The slot 25 is limited in the circumferential direction by the transversal walls of the cut-out. In the radial direction the slot 25 is limited, on its inner side, by the circumferential wall of the cut-out. On its outer side the slot 25 is substantially limited by the flexible arm 32. However, the arm 32 extends only partly along the outer circumferential edge of the slot 25, defining in the circumferential direction, a closed end 21 of the slot and an open end 23 of the slot, FIG. 4, forming a gap between the ledge 34 and one of the transversal walls of the slot 25.

The at least one dose reset member 18 comprises a first arm portion 20 protruding generally transversal to the outer circumferential surface of said dose setting member 10, and a second arm portion 22 axially extending towards the proximal direction, and wherein said second arm portion is arranged with a curved surface 24. A supporting element 17, comprises a first portion protruding generally transversal to the outer circumferential surface of said dose setting member 10, and a second portion axially extending towards the proximal direction into the slot 25, abutting the flexible arm 32. The supporting element 17 is arranged next to the dose reset member 18, but separated from the latter by a predetermined distance along the circumference of said dose setting member 10.

Each ledge 34 on the flexible arms 32 of the connection member 26 is arranged with one side surface 36 having a curved shape and arranged to cooperate with the curved surface 24 of the second arm portion 22 of the reset member 18.

The engagement means comprises at least one dose setting drive member 16 having a first part protruding generally transversal to the outer circumferential surface of said dose setting member 10 and a second part axially extending towards the proximal direction, and at least one cut-out 30 provided on the outer circumferential surface connection member 26 such that the position of said at least one cut-out correspond to the positions of the at least one drive members, whereby the drive members fit into the cut-outs.

The dose setting member 10 shown in the example of FIG. 2 comprises a generally tubular body 12. The distal end of the tubular body protrudes through a distal end of the medicament delivery device, which distal end is attached to, or integral with, the dose setting knob 14.

Figure 3:
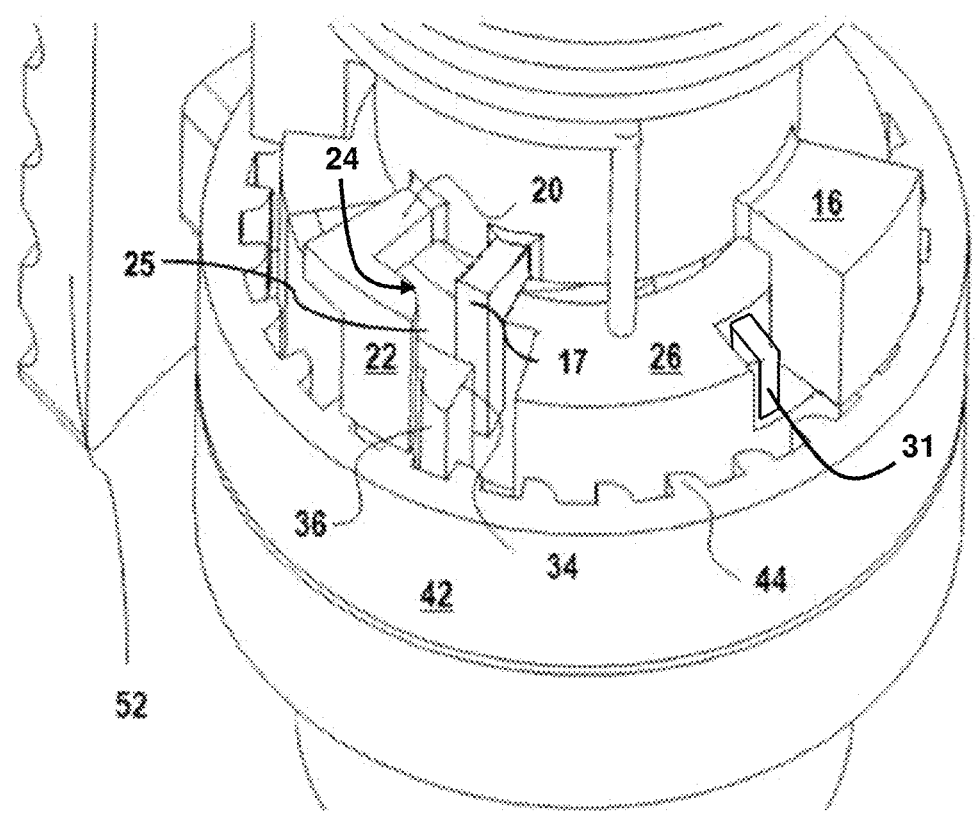
FIG. 3 is a detailed view of the dose reset mechanism in an initial state.

In the example shown in FIG. 2, at the proximal end of the dose setting member 10, two dose setting drive members 16 are attached to, or integral with, the outer circumferential surface and positioned generally opposite to each other. The dose setting drive members 16 are designed as rectangular ledges having a first part protruding generally transversal to the outer circumferential surface and a second part extending in the proximal direction. In the example shown in FIG. 2, two dose reset members 18 are also attached to, or made integral with, the outer circumferential surface and positioned generally opposite each other. The dose reset members are designed as a first arm portion 20 protruding generally transversal to the outer circumferential surface, and a second arm portion 22 extending in the proximal direction. The second arm portion is arranged with a curved surface 24. In the same manner, two supporting elements 17 may be arranged generally opposite each other, next to the respective dose reset members 18, with a first portion protruding generally transversal to the outer circumferential surface, and a second portion extending in the proximal direction into the slots 25, but separated from the dose reset members 18 by a predetermined distance along the circumferential direction of the dose setting member 10, FIG. 3.

The connection member 26 is arranged at the proximal end of the dose setting member. The connection member comprises a generally ring-shaped member 28 having a certain width in the longitudinal direction as well as a certain thickness in the radial direction. In the example shown in FIG. 2, two cut-outs 30 are provided in the connection member 26 in the transition region between the distal side surface and the outer circumferential surface of the connection member and generally opposite each other such that the positions of the cut-outs 30 correspond to the positions of the dose setting drive members 16, whereby the drive members fit into the cut-outs. However, the width of the cut-outs 30 as seen in the circumferential direction is somewhat larger than the width of the dose setting drive members 16 as seen in the circumferential direction. At least one flexible return element 31 (see FIG. 3) is circumferentially arranged in the cut-outs 30, between at least one transversal wall of the cut-outs 30 and the dose setting driver members 16, in order to resiliently bias the dose setting member 10 towards a predetermined, neutral, position when the dose setting member 10 is at rest.

The neutral position of the dose setting member 10 is generally defined as the predetermined positions of the supporting elements 17, adjacent the radial outwardly protruding ledges 34 at which the forces of the return elements acting on the dose setting drive members 16, and consequently on the dose setting member 10, are at equilibrium. Equilibrium is attained when external rotational forces acting on the dose setting knob 14, and consequently on the dose setting member 10, equal zero.

In the example shown in FIG. 2, the connection member 26 is further arranged with two flexible arms 32 extending in the circumferential direction of the member and positioned generally opposite each other. The ends of the arms 32 are arranged with generally radial outwardly protruding ledges 34, FIG. 3. Each ledge is arranged with one side surface 36 having a curved shape and arranged to cooperate with the curved surface 24 of the second arm portion 22 of the reset member 26, FIG. 3.

The drive member 38 comprises a generally tubular body 40 where the inner surface is arranged with threads, which threads are arranged to cooperate with corresponding threads on a plunger rod 41. A ring-shaped portion 42 is attached, or made integral with, the distal end of the body 40. The inner circumferential surface of the ring-shaped portion is arranged with a number of generally radial inwardly extending ledges 44. The ledges have a shape such that one side surface is made generally planar and the other side surface is arranged curved. The ledges are arranged to cooperate with the ledges 34 of the arms 32 as a type of ratchet in a manner that will be described.

Further, the outer circumferential surface of the body 40 adjacent the ring-shaped portion 42 is arranged with a number of longitudinally extending ledges or splines 46, FIG. 2, which are arranged to cooperate with corresponding ledges or splines (not shown) arranged on the inner circumferential surface of a ring-shaped member 48 of an actuator 50, FIG. 1. The actuator is provided with a slide button 52 attached to, or made integral with, the ring-shaped member. Further a drive spring 54, in the shown embodiment a torsion spring, is attached between the connection member 26 and a fixed part of the medicament delivery device, such as e.g. the housing.

The mechanism is intended to function as follows. When a dose is to be set for the delivery of a certain quantity of medicament, the dose setting knob 14 is turned, in the clockwise direction of the drawings. Because of the connection between the dose setting member 10 and the connection member 26 by the dose setting drive members 16 fitting into the cut-outs 30, the connection member 26 is also turned. Because the cut-outs 30 in the connection member 26 are larger in width than the dose setting drive members 16, the dose setting member 10 is movable between the neutral position and a dose setting position in which the supporting element 17 is positioned in the closed end 21 of the slot. During this initial phase the supporting elements 17 are displaced within the slots 25 towards the closed ends 21 to allow free radial movement of the ledges 34 of the arms 32. When the connection members 26 start turning, i.e. when the dose setting member 16 starts to exert a force on the transversal walls of the cut-outs 30, the ledges 34 begin to slide over the corresponding ledges 44 on the drive member, providing distinct click sounds. The turning also causes the torsion spring 54 to be tensioned.

If the dose knob 14 is released, the dose setting member 10, and consequently the supporting elements 17, are returned to their initial, neutral, positions wherein the supporting elements 17 rest in the slots 25, adjacent the ledges 34, by means of the flexible return members (not shown) arranged in the cut-outs 30 to bias the dose setting member towards its predetermined, neutral, position. The position of the connection element 26 is maintained in that the planar surfaces of the ledges 34 of the arms 32 abut the planar surfaces of the ledges 44 of the drive member and in that the positions of the supporting elements 17, abutting the ledges 34, prevent any accidental disengagement of the ledges 34 from the ledges 44.

Figure 5:
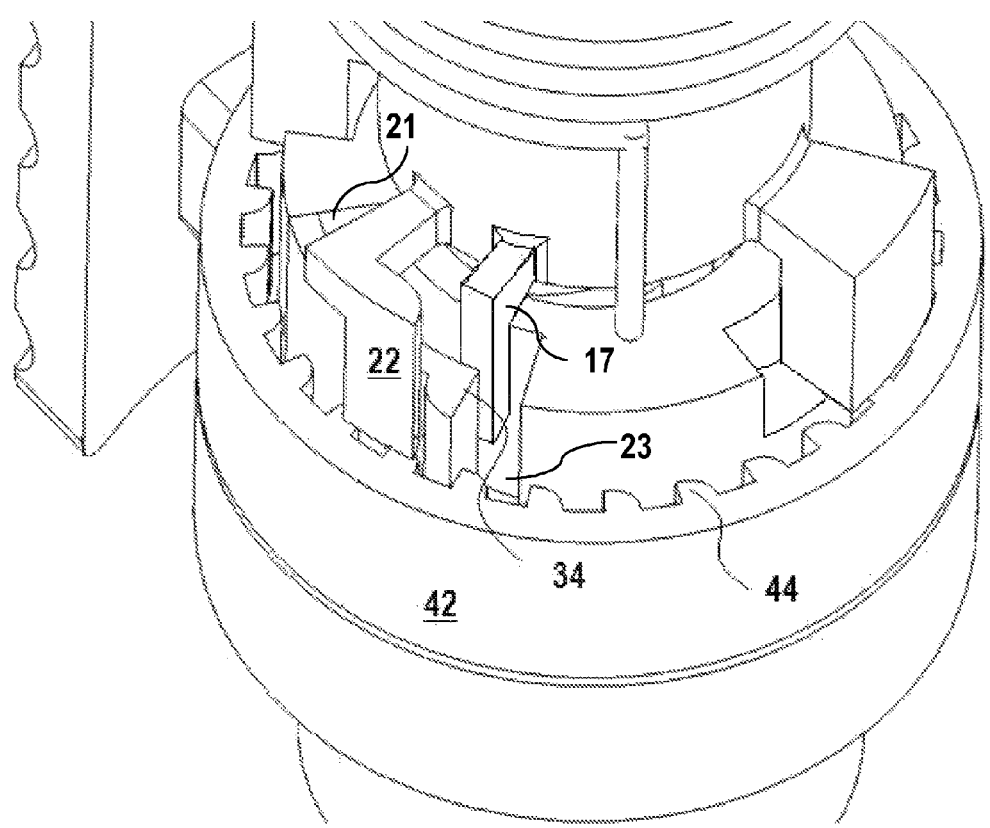
FIG. 5 is a detailed view of the dose reset mechanism when the reset movement is completed.

Should the user by accident turn the dose setting knob such that a too large dose is set, the dose setting has to be reset. With the present invention this is performed by merely turning the dose knob 14 in the counter-clockwise direction. Because the cut-outs 30 in the connection member 26 are larger in width than the dose setting drive members 16, the dose setting member 10 is movable between the neutral position in which the supporting element 17 is positioned in the slot 25 adjacent the outwardly protruding ledges 34 and a reset position in which the supporting element 17 is positioned in the gap at the open end 23 of the slot. The connection member 26 is still held in position by the ledges 34 of the arms 32 engaging the ledges 44 of the drive member 38. During the anti-clockwise movement of the dose setting member 10, the supporting elements 17 will be displaced into the open ends 23 of the slots 25 whereby the arms 32 are free to flex radially inwards. The second arm portion 22 of the dose reset member 18 will then come in contact with the ledges 34 of the arms 32 such that the corresponding curved surfaces abut. Further movement in combination with the curved surfaces will cause the free ends of the arms 32 to be moved radially inwards until the ledges 34 of the arms move out of contact with the ledges 44 of the drive member 38, FIG. 4. Due to the force of the drive spring 54, the connection member 26 is moved in the anti-clockwise direction, whereby the ledges 34 of the arms 32 loose contact with the second portion 22 of the dose reset member 18. The arms 32 are then free to flex back outwards in the radial direction, whereby the ledges 34 of the arms come in contact with the subsequent ledge 44 of the drive member 38 and the rotation is stopped. If the user releases the dose setting knob the supporting elements 17 are returned to the neutral position inside the slots 25, adjacent the ledges 34, due to the return elements (not shown) arranged in the cut-outs 30, FIG. 5. The procedure can be performed until the prescribed dose is set. Thus the reset procedure is performed one step at the time.

When a dose is to be delivered, the actuator 50 is pushed in the longitudinal direction such that the splines of the ring-shaped member 48 are moved out of contact with the splines 46 of the drive member 38, wherein the latter is free to rotate together with the connection member 26 due to the connection between the two via the arms of the connection member abutting the ledges of the drive member. The rotation of the drive member causes the plunger rod 41 to be moved forward due to the threaded connection between the plunger rod 41 and the drive member 38.

It is to be understood that the invention described above and shown in the drawings is to be regarded only as a non-limiting example of the invention and that it may be modified in many ways within the scope of the patent claims.

The invention claimed is:

1. A dose reset mechanism for a medicament delivery device having a housing having opposite distal and proximal ends and a medicament container, comprising:

a dose setting member coaxially and rotationally arranged in the housing for setting a dose when it is rotated and for resetting the dose when it is rotated in an opposite direction, the dose setting member having a dose setting knob accessible outside the distal end of the housing;

a drive member connected to a plunger rod to act on the container for expelling the medicament;

a connection member arranged between the dose setting member and the drive member, wherein the connection member and the dose setting member are connected by an engagement mechanism, and the connection member and the drive member are connected by a ratchet mechanism such that the connection member rotates when the dose setting knob rotates for setting a dose and is prevented by the ratchet mechanism from moving in the opposite direction; and a drive spring having a first end connected to the connection member and a second end connected to a fixed point of the housing such that the drive spring is tensioned when the dose setting member and the connection member are rotated for setting a dose;

wherein the dose setting member further has at least one dose reset member and at least one supporting element interactively connected to the ratchet mechanism such that the ratchet connection between the connection member and the drive member is released when the dose knob is turned in the opposite direction; and the at least one dose reset member comprises a first arm portion protruding generally transverse to an outer circumferential surface of the dose setting member, a second arm portion axially extending in a proximal direction, and the second arm portion includes a curved surface.

2. The dose reset mechanism of claim 1, wherein the drive member is threadedly connected to the plunger rod such that when the drive member is rotated, the plunger rod is axially moved to expel the medicament.

3. The dose reset mechanism of claim 1, wherein the ratchet mechanism comprises a number of generally radial inwardly extending ledges on a distal inner circumferential surface of the drive member, and generally radial outwardly protruding ledges on free ends of flexible arms extending in a circumferential direction of the connection member.

4. The dose reset mechanism of claim 3, wherein the connection member comprises at least one cut-out forming a slot that extends in a circumferential direction of the connection member and is limited in the circumferential direction by transversal walls of the at least one cut-out and in the radial direction by the circumferential wall of the cut-out and by the flexible arm.

5. The dose reset mechanism of claim 4, wherein the at least one cut-out comprises a closed end from which the flexible arm extends and an open end forming a gap between the ledge and one of the transversal walls of the slot.

6. The dose reset mechanism of claim 1, wherein each ledge on the flexible arms of the connection member is arranged with one side surface having a curved shape and to cooperate with the curved surface of the second arm portion of the reset member.

7. The dose reset mechanism of claim 1, wherein the engagement mechanism comprises at least one dose setting drive member having a first part protruding generally transverse to the outer circumferential surface of the dose setting member and a second part axially extending in a proximal direction, and at least one cut-out provided on the outer circumferential surface of the connection member such that a position of the at least one cut-out corresponds to a position of the at least one drive member, whereby the drive member fits in the cut-outs.

8. The dose reset mechanism of claim 7, wherein a width of the at least one cut-out is larger than a width of the at least one drive member.

9. The dose reset mechanism of claim 8, wherein flexible return elements are circumferentially arranged in the cut-outs, between at least one transversal wall of the cut-outs and the dose setting drive members, and are configured for returning the dose setting member to a neutral position.

10. The dose reset mechanism of claim 1, wherein the dose reset mechanism is included in a medicament delivery device.

11. A dose reset mechanism for a medicament delivery device having a housing having opposite distal and proximal ends and a medicament container, comprising:
- a dose setting member coaxially and rotationally arranged in the housing for setting a dose when it is rotated and for resetting the dose when it is rotated in an opposite direction, the dose setting member having a dose setting knob accessible outside the distal end of the housing;
- a drive member connected to a plunger rod to act on the container for expelling the medicament;
- a connection member arranged between the dose setting member and the drive member, wherein the connection member and the dose setting member are connected by an engagement mechanism, and the connection member and the drive member are connected by a ratchet mechanism such that the connection member rotates when the dose setting knob rotates for setting a dose and is prevented by the ratchet mechanism from moving in the opposite direction; and
- a drive spring having a first end connected to the connection member and a second end connected to a fixed point of the housing such that the drive spring is tensioned when the dose setting member and the connection member are rotated for setting a dose;

wherein the dose setting member further has at least one dose reset member and at least one supporting element interactively connected to the ratchet mechanism such that the ratchet connection between the connection member and the drive member is released when the dose knob is turned in the opposite direction;

the ratchet mechanism comprises a number of generally radial inwardly extending ledges on a distal inner circumferential surface of the drive member, and generally radial outwardly protruding ledges on free ends of flexible arms extending in a circumferential direction of the connection member;

the connection member comprises at least one cut-out forming a slot that extends in a circumferential direction of the connection member and is limited in the circumferential direction by transversal walls of the at least one cut-out and in the radial direction by the circumferential wall of the cut-out and by the flexible arm; and at least one supporting element having a first portion protruding generally transversal to the outer circumferential surface of the dose setting member and a second portion axially extending toward the proximal direction into the slot is configured for locking outwardly protruding ledges in engagement with inwardly extending ledges when the supporting element is positioned adjacent the outwardly protruding ledges.

12. The dose reset mechanism of claim 11, wherein the dose setting member is movable between a neutral position, in which the supporting element is positioned in the slot adjacent the outwardly protruding ledges, and a reset position, in which the supporting element is positioned in the gap at the open end of the slot.

13. The dose reset mechanism of claim 12, wherein the dose setting member is movable between the neutral position and a dose setting position, in which the supporting element is positioned in the closed end of the slot.

* * * * *